United States Patent
Chaudry

(10) Patent No.: US 8,158,154 B2
(45) Date of Patent: *Apr. 17, 2012

(54) NASAL PHARMACEUTICAL FORMULATIONS AND METHODS OF USING THE SAME

(75) Inventor: Imtiaz Chaudry, Napa, CA (US)

(73) Assignee: Dey Pharma, L.P., Basking Ridge, NJ (US)

( * ) Notice: Subject to any disclaimer, the term of this patent is extended or adjusted under 35 U.S.C. 154(b) by 1113 days.

This patent is subject to a terminal disclaimer.

(21) Appl. No.: 11/931,424

(22) Filed: Oct. 31, 2007

(65) Prior Publication Data

US 2008/0058295 A1    Mar. 6, 2008

Related U.S. Application Data

(63) Continuation of application No. 10/414,756, filed on Apr. 16, 2003, now Pat. No. 7,811,606.

(51) Int. Cl.
*A61K 9/14*    (2006.01)
(52) U.S. Cl. ...................................................... 424/489
(58) Field of Classification Search ................ None
See application file for complete search history.

(56) References Cited

U.S. PATENT DOCUMENTS

| | | | |
|---|---|---|---|
| 3,091,569 | A | 5/1963 | Sheffner |
| 5,174,475 | A | 12/1992 | Day et al. |
| 5,593,688 | A | 1/1997 | Baldeschwieler |
| 5,858,330 | A | 1/1999 | Boltri et al. |
| 5,976,573 | A | 11/1999 | Kim |
| 5,993,781 | A | 11/1999 | Snell et al. |
| 6,113,894 | A | 9/2000 | Smith |
| 6,207,703 | B1 | 3/2001 | Ponikau |
| 6,241,969 | B1 | 6/2001 | Saidi et al. |
| 6,291,500 | B2 | 9/2001 | Ponikau |
| 6,368,616 | B1 | 4/2002 | Doi |
| 6,410,062 | B1 | 6/2002 | Callaghan et al. |
| 6,464,958 | B1 | 10/2002 | Bernini et al. |
| 6,465,709 | B1 | 10/2002 | Sun et al. |
| 6,509,028 | B2 | 1/2003 | Williams et al. |
| 6,555,566 | B2 | 4/2003 | Ponikau |
| 6,608,054 | B2 | 8/2003 | Meade et al. |

(Continued)

FOREIGN PATENT DOCUMENTS

EP    0 343 268    11/1989

(Continued)

OTHER PUBLICATIONS

Russian Office Action for Russian Application No. 2005 135 333 dated Sep. 18, 2009.

(Continued)

*Primary Examiner* — Carlos Azpuru
(74) *Attorney, Agent, or Firm* — Alston & Bird LLP

(57) ABSTRACT

Nasal pharmaceutical formulations comprising a drug substance having a specific particle size distribution profile are disclosed herein. Such profile provides increased bioavailability, increased efficacy or prolonged therapeutic effect of the drug substance when administered intranasally. The formulations of the present invention may comprise one or more corticosteroids having a specific particle size distribution profile. In a preferred embodiment, the corticosteroid is beclomethasone or a pharmaceutically acceptable derivative thereof for the treatment of one or more symptoms of rhinitis. Preferably, the drug substance is beclomethasone dipropionate. The formulations herein may be provided as an aqueous suspension suitable for inhalation via the intranasal route.

8 Claims, 4 Drawing Sheets

U.S. PATENT DOCUMENTS

| | | | |
|---|---|---|---|
| 7,811,606 B2 * | 10/2010 | Chaudry | 424/499 |
| 2001/0002404 A1 | 5/2001 | Webb et al. | |
| 2002/0006944 A1 | 1/2002 | Ohkawa et al. | |
| 2002/0010208 A1 | 1/2002 | Shashoua et al. | |
| 2002/0013331 A1 | 1/2002 | Williams et al. | |
| 2002/0052390 A1 | 5/2002 | Ponikau | |
| 2002/0061281 A1 | 5/2002 | Osbakken et al. | |
| 2002/0071874 A1 | 6/2002 | Olejnik et al. | |
| 2002/0124820 A1 | 9/2002 | Kreuter | |
| 2002/0136918 A1 | 9/2002 | Akutsu et al. | |
| 2002/0177609 A1 | 11/2002 | Swindell et al. | |
| 2002/0192288 A1 | 12/2002 | Williams et al. | |
| 2002/0198209 A1 | 12/2002 | Woodward et al. | |
| 2003/0017199 A1 | 1/2003 | Woodward et al. | |
| 2003/0065023 A1 | 4/2003 | Swindell et al. | |
| 2004/0045805 A1 | 3/2004 | Lancaster et al. | |
| 2004/0081626 A1 | 4/2004 | Watanabe et al. | |
| 2004/0136918 A1 | 7/2004 | Garrett et al. | |
| 2004/0141925 A1 | 7/2004 | Bosch et al. | |
| 2007/0140980 A1 | 6/2007 | Capocchi et al. | |
| 2008/0050442 A1 | 2/2008 | Chaudry | |

FOREIGN PATENT DOCUMENTS

| | | |
|---|---|---|
| EP | 0 385 445 A2 | 9/1990 |
| JP | 1-100120 A | 4/1989 |
| JP | 03-165833 | 7/1991 |
| JP | 5-506642 | 9/1993 |
| JP | 07-053358 | 2/1995 |
| JP | 11-130659 A | 5/1999 |
| JP | 11-514979 A | 12/1999 |
| JP | 2000-508675 A | 7/2000 |
| JP | 2001-002589 | 1/2001 |
| JP | 2001-520188 A | 10/2001 |
| JP | 2001-523638 | 11/2001 |
| JP | 2002-539154 | 11/2002 |
| JP | 2003-506396 | 2/2003 |
| JP | 2005-503378 | 2/2005 |
| JP | 2005-506369 | 3/2005 |
| WO | WO 86/03750 | 7/1986 |
| WO | WO 92/04365 | 8/1992 |
| WO | WO 92/17183 | 10/1992 |
| WO | WO 97/08950 A1 | 3/1997 |
| WO | WO 99/18971 | 4/1999 |
| WO | WO 00/12063 A1 | 3/2000 |
| WO | WO 00/25746 | 5/2000 |
| WO | WO 00/27363 | 5/2000 |
| WO | WO 01/10409 A1 | 2/2001 |
| WO | WO 01/13885 A1 | 3/2001 |
| WO | WO 01/32125 | 5/2001 |
| WO | WO 01/49263 | 7/2001 |
| WO | WO 01/78743 A1 | 10/2001 |
| WO | WO 02/00199 | 1/2002 |
| WO | WO 02/055136 A2 | 7/2002 |
| WO | WO 02/072066 A1 | 9/2002 |
| WO | WO 03/013434 A2 | 2/2003 |
| WO | WO 03/020219 A2 | 3/2003 |
| WO | WO 03/035062 A1 | 5/2003 |

OTHER PUBLICATIONS

Bernstein, I. L., *Is the Use of Benzalkonium Chloride as a Preservative for Nasal Formulations a Safety Concern? A Cautionary Note Based on Compromised Mucociliary Transport*, J. Allergy Clin. Immunol., 105(1), Jan. 2000, pp. 39-44.

Office Action for Japanese Application No. 2006-504903 dated Aug. 4, 2010.

Office Action for Japanese Application No. 2006-504901 dated Aug. 4, 2010.

Office Action for Japanese Application No. 2006-504902 dated Aug. 4, 2010.

Office Action for Japanese Application No. 2006-516000 dated Sep. 8, 2010.

Lacy et al., 1999-2000 Drug Information Handbook, Lexi-Comp, Inc., 1999, pp. 561-563 and 568-569.

Hebrecht et al., "Voriconazole versus amphotericin B for primary therapy of invasive aspergillosis", N.Eng. J. Med., 2002, 347(6), pp. 408-415.

Americas Family Physician—Jan. 1, 2001—Adult Rhinosinusitis: Diagnosis and Management—J. David Osguthorpe, M.D., Medical University of South Carolina, Charleston, South Carolina—http://www.aafp.org/afp/20010101/69.html.

The Diagnosis and Incidence of Allergic Fungal Sinusitis—Jens U. Ponikau, MD; David A. Sherris, MD; Eugene B. Kern, MD; Henry A. Homburger, MD; Evangelos Frigas, MD; Thomas A. Gaffey, MD; and Glenn D. Robers, PhD—1999 Mayo Foundation for Medical Education and Research—May Clin. Proc, Sep. 1999, vol. 74.

Mayo Clinic, Rochester Minnesota—Mayo Clinic Receives Patent for New Treatment of Chronic Sinus Infection Apr. 30, 2003—http://www.mayclinic.org/news2003-rst/1772.html.

NCBI—PubMed—Improved method for estimation of azole antifungal inhibitory concentrations against *Candida* Species, based on azole/antibiotic interactions; Odds FC, Abbot AB, Pye G., Troke PF.; Mar. 17, 2003.

Invasive *Aspergillus rhinosinusitis* in patients with acute leukemia (Mar.-Apr. 13, 1991) http://www.ncbi.nlm.nih.gov/entrez/query.fcgi?cmd_Retrieve&db=PubMed&List_uids-19.

Efficacy of Sch39304 in murine cyptococcosis (Aug. 1989) http://www.ncbi.nlm.nih.gov/entrez/query.fcgi?cmd_Retrieve&db=PubMed&List_uids-25.

Drug Information Handbook, C. Lacy et al., Lexi-Comp, Inc., Cleveland, 1993, pp. 397.

Lacy, C. et al., 1999-2000 Drug Information Handbook, Lexi-Comp, Inc., Cleveland, 1999, pp. 112-114.

Lacy, C. et al., Drug Information Handbook, Lexi-Comp, Inc., Cleveland, 1999, pp. 445-446.

Flonase® from the online Physician's Desk Reference (PDR®)—accessed Dec. 1, 2007.

"Beconase AQ®" from the online Physician's Desk Reference (PDR®)—accessed Nov. 19, 2007.

Chervinsky, P., "Clinical Review of Once-Daily Beclomethasone Dipropionate for Seasonal Allergic Rhinitis", Clinical Therapeutics, 1996, 18(5), pp. 790-796.

Lacy et al., 1999-2000 Drug Information Handbook, Lexi-Comp, Inc., Aug. 21, 1999, 26-28, 225-226, 453-456, 463-464 and 721-722.

Walker, Management of Allergic Rhinitis, Nursing Times, Aug. 21, 2003, 99(23).

Humuy et al., Topical Antiviral Agents for Herpes Simplex Virus Infections, Drugs Today, Aug. 21, 1998, 34(12).

Vippagunta et al., Crystalline Solids, Advanced Drug Delivery Reviews, Aug. 21, 2001, 3-26, 48.

Merriam-Webster's Collegiate Dictionary, $10^{th}$ edition, Merriam-Webster Incorporated: Springfield, Massachusetts, 1993 p. 311.

Office Action dated Jul. 12, 2010, and issued in connection with corresponding Canadian Application No. 2,522,294.

Office Action mailed Aug. 6, 2010, and issued in connection with corresponding U.S. Appl. No. 10/657,550.

Parikh, A., et al.; Topical corticosteroids in chronic rhinosinusitis: a randomized, double-blind, placebo-controlled trial using fluticasone propionate aqueous nasal spray; Rhinology, 39; 2001; pp. 75-79.

* cited by examiner

NASAL PHARMACEUTICAL FORMULATIONS AND METHODS OF USING THE SAME

CROSS REFERENCE TO RELATED APPLICATIONS

This application is a continuation of Ser. No. 10/414,756, filed Apr. 16, 2003 now U.S. Pat. No. 7,811,606, which is hereby incorporated herein in it entirety by reference.

I. FIELD OF THE INVENTION

The present invention is directed to nasal pharmaceutical formulations comprising a drug substance having a specific particle size distribution profile. Such profile provides increased bioavailability, increased efficacy or prolonged therapeutic effect of the drug substance when administered intranasally. In an alternative embodiment, formulations of the present invention comprise a beclomethasone or a pharmaceutically acceptable derivative thereof having a specific particle size distribution profile. The formulation may be provided as an aqueous suspension suitable for intranasal administration to a subject in need thereof.

II. BACKGROUND OF THE INVENTION

It is known that the particle size of a drug substance affects bioavailability of the drug and efficacy. Methods of making finely divided drugs have been studied and efforts have been made to control the size and size range of drug particles in pharmaceutical compositions. However, the prior art does not disclose drug substances having specific particle size distribution profiles which provide increased bioavailability, increased efficacy or prolonged therapeutic effect of the drug when administered intranasally.

It is known that inhaled corticosteroids are one of the most effective anti-inflammatory medications used in the treatment of respiratory disorders or diseases characterized by inflammation. One such corticosteroid, beclomethasone dipropionate (BDP), is particularly useful in the treatment or prophylaxis of seasonal or perennial rhinitis and is also indicated for the relief of one or more symptoms associated with seasonal or perennial allergic and non-allergic (vasomotor) rhinitis. Rhinitis is a reaction that occurs in the eyes, nose and throat when airborne irritants, for example, trigger the release of histamine. Histamine causes inflammation and fluid production in the fragile linings of nasal passages, sinuses and eyelids. Use of corticosteroids such as beclomethasone can cause partial or whole relief from rhinitis-related symptoms such as sneezing, congestion, runny nose, itchy nose, throat eyes and ears. Use of beclomethasone can also delay the recurrence of nasal polyps in individuals who have undergone nasal polyopectomy. In those polyps that do recur, beclomethasone can suppress the polyp's growth increase in size.

Like most corticosteroids and other drug substances, BDP is very slightly soluble in water. When such drug substances are administered intranasally, they are typically suspended in an aqueous solution. However, when these substances are administered intranasally via a conventional nasal spray, less than optimal amounts of drug substance is absorbed by the nasal mucosa (the target tissue), with the remainder being swallowed or expelled from the nasal cavity. In some instances, particles which are not sufficiently small are eliminated from the gastrointestinal tract before being disposed onto the target area. The inability to administer optimal amounts of a drug substance results in reduced bioavailability and efficacy of that drug substance.

III. SUMMARY OF THE INVENTION

The present invention is directed to a nasal pharmaceutical formulation comprising a drug substance having a specific particle size distribution profile which provides increased bioavailability, increased efficacy or prolonged therapeutic effect of the drug substance when administered intranasally. Specifically, in one alternative embodiment, the formulation of the present invention comprises a drug substance (e.g., active ingredient) having the following particle size distribution profile: about 10% of the drug substance particles have a particle size of about 0.75 microns; about than 25% of the drug substance particles have a particle size of less than 1.5 microns; about 50% of the drug substance particles have a particle size of less than 2.0 microns; about 75% of the drug substance particles have a particle size of less than 3.5 microns; about 90% of the drug substance particles have a particle size of less than 5.0 microns; and, greater than 90% or about 100% of the drug substance particles have a particle size of less than 10 microns. In one alternative embodiment, the drug substance is a corticoid steroid, preferably beclomethasone or a pharmaceutically acceptable derivative thereof.

IV. FIGURES

V. DETAILED DESCRIPTION OF THE INVENTION

Figure 1:
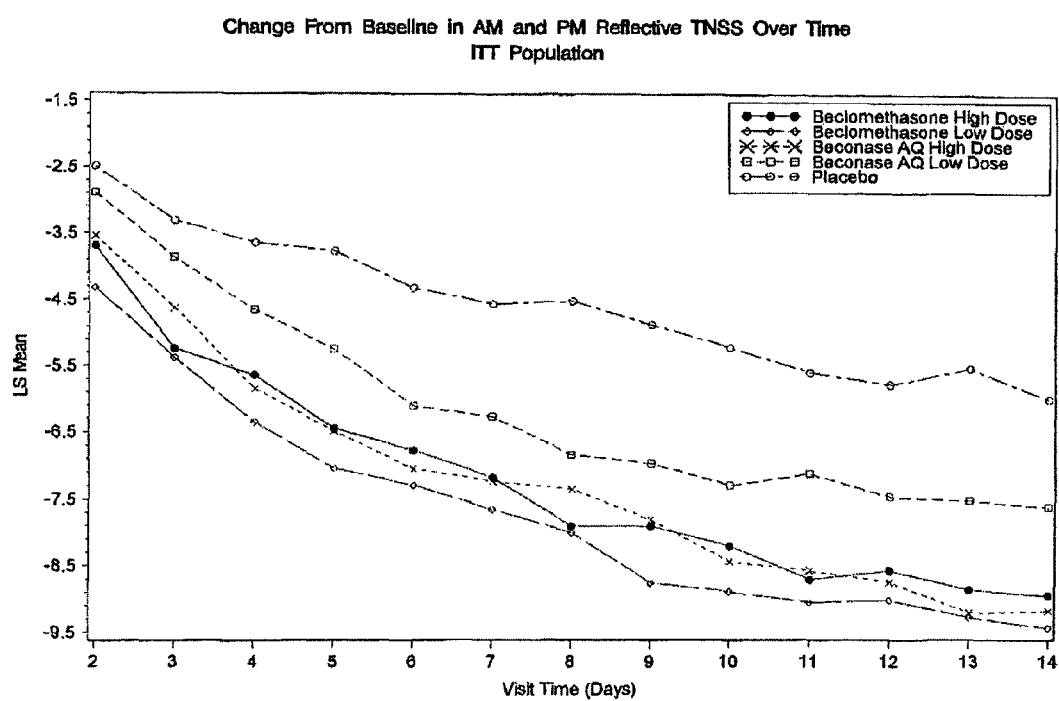
FIG. 1 shows the change from baseline in AM and PM reflective TNSS over time in the ITT population over a 14 day study period.

The formulations provided herein are used for treating, preventing and/or ameliorating one or more symptoms of a medical condition, disorder or disease. As used herein, treatment means any manner in which one or more of the symptoms of the condition, disorder or disease are ameliorated or otherwise beneficially altered. Treatment also encompasses any pharmaceutical or medicinal use of the formulations herein. As used herein, amelioration of the symptoms of a particular disorder by administration of a particular formulation refers to any lessening, whether permanent or temporary, lasting or transient that can be attributed to or associated with administration of the formulation. As used herein, a "therapeutic effective amount" means a sufficient amount of drug substance to treat, prevent and/or ameliorate one or more symptoms of a medical condition, disorder or disease. It also may include a safe and tolerable amount of drug substance, as based on industry and/or regulatory standards.

In one alternative embodiment, the formulations provided herein are used for treating, preventing and/or ameliorating one or more symptoms of a respiratory disorder in an individual. In another alternative embodiment, the present invention provides a formulation for the treatment, prophylaxis and/or amelioration of one or more symptoms of rhinitis or other related disorders, wherein the formulation comprises one or more corticosteroids having a specific particle size distribution profile. In an alternative embodiment, the drug substance is beclomethasone or a pharmaceutically acceptable derivative thereof. Preferably, the drug substance is beclomethasone dipropionate. Surprisingly, it has been found that a drug substance having the present particle size distribution profiles, when administered intranasally to a subject in need thereof, provides increased bioavailability of the drug substance, as well as increased and prolonged efficacy when compared to conventional formulations containing the same drug substance. Drug substances for use herein include any pharmaceutical compound having the present particle size distribution profile and capable of treating, preventing and/or amelioration one or more symptoms of a medical condition, disorder or disease when such substance is administered intranasally to a subject in need thereof.

Mode of Administration

The present formulations may be packaged for administration in any conventional manner, preferably in a nasal applicator, and preferably in such a way as to deliver a fixed dose of drug substance (e.g., active ingredient). However, the present formulations may be administered via a nasal application in such a way as to deliver a non-fixed dose of drug substance. Spray Administration containers for various types of nasal formulations have been known in the past and substantially all will be equally suitable for the present formulations, considering of course that the materials from which the container is made is compatible with the formulations. The medium containing the drug substance and other appropriate ingredients may be contained in a small bottle or similar container, from which it can be dispersed as a mist to be directed into each nostril. Using ambient air as the propelling agent, one may have the bottle made of a flexible plastic, so that merely squeezing the bottle's sides impels the spray out through the nozzle into the nasal cavity. Air may also be the propelling agent for a pump sprayer, in which the user manipulates a small pump button which pumps air into the container and causes the liquid spray to be emitted on the return stroke. Alternatively, the bottle can be pressurized with a gas which is inert to the user and to the ingredients of the solution. The gas may be dissolved under pressure in the container or may be generated by dissolution or reaction of a solid material which forms the gas as a product of dissolution or as a reaction product. Typical gases which can be used include nitrogen, argon, and carbon dioxide. Also, when the formulation is administered as a spray or aerosol, the formulation may be contained in a pressurized container with a liquid propellant including, but not limited to dicholorodifluoro methane or chlorotrifluoro ethylene, among other propellants.

In another alternative embodiment, for administration as a spray, the present formulations may be placed in an appropriate atomizing device, e.g. in a pump-atomiser or the like. The atomizing device may be provided with appropriate means for delivery of aqueous spray to the naris. Preferably, it is provided with means ensuring delivery of a substantially fixed volume of composition/actuation (i.e. per spray-unit). In one embodiment, the device administers a metered dosage. The spray composition may be suspended or dissolved in a liquid propellant. Stabilizing and/or suspending agents and/or co-solvents may be present. In other embodiments herein, the formulation of the present invention is suitable for administration intranasally via a metered-dose spray pump to a subject in need thereof. In this respect, the formulation of the present invention may be pre-packaged in a metered-dose spray pump bottle, or metering atomizing pump.

In another alternative embodiment, the formulations of the present invention may be administered into the nose in the form of drops, or any other method which results in topical application to the nasal mucosa. The form of dosage for intranasal administration may include solutions, suspensions or emulsions of the active compound in a liquid carrier in the form of nose drops. Suitable liquid carriers include water, propylene glycol and other pharmaceutically acceptable alcohols. For administration in drop form formulations may suitably be put in a container provided e.g. with a conventional dropper/closure device, e.g. comprising a pipette or the like, preferably delivering a substantially fixed volume of composition/drop. The dosage forms may be sterilized, as required. The dosage forms may also contain adjuvants such as preservatives, stabilizers, emulsifiers or suspending agents, wetting agents, salts for varying the osmotic pressure or buffers, as required.

In another alternative embodiment, the present formulations may be administered in the form of a powder. For example, a powdery nasal composition can be directly used as a powder for a unit dosage form. If desired, the powder can be filled in capsules such as hard gelatine capsules. The contents of the capsule or single dose device may be administered using e.g. an insufflator. Preferably, it is provided with means ensuring dosing of a substantially fixed amount of composition/actuation.

Drug Substance

The present invention is directed to formulations for the treatment, prophylaxis, or amelioration of one or more symptoms of a condition, disorder or disease. In alternative embodiment, the present invention is directed to formulations for the treatment, prophylaxis, or amelioration of one or more symptoms of rhinitis or any other respiratory disorder. For example, the formulations disclosed herein are useful for the treatment of seasonal allergic rhinitis (e.g., hay fever) or perennial allergic and nonallergic (vasomotor) rhinitis.

Drug substances suitable for use in the present formulations include any pharmaceutical-acceptable compound company or any of its derivatives including, but not limited to, any salts, esters, enol, esters, enol esters, acids, bases, solvates or hydrates thereof. Such derivatives may be prepared by those of skill in the art using known methods for such derivatization. Further, the drug substances for use in the formulations and methods provided herein include those compounds comprising chiral centers of either the (R) or (S) configuration, or a mixture thereof (e.g., racemate). Thus, the drug substances for use in the compositions provided herein include enantiomerically pure compounds, or stereoisomeric or diastereomeric mixtures thereof. It is to be understood that the chiral centers of the drug substances provided herein may undergo epimerization in vivo. Thus, one of skill in the art will recognize that administration of a drug substance in its (R) form is equivalent, for compounds that undergo epimerization in vivo, to administration of the compound in its (S) form.

Drug substances suitable for use in the present formulations include, but are not limited to, corticosteroids, such as beclomethasone and any of its pharmaceutically acceptable derivatives. As used herein, pharmaceutically acceptable derivatives of a beclomethasone include any salts, esters, enol ethers, enol esters, acids, bases, solvates or hydrates thereof. Such derivatives may be prepared by those of skill in the art using known methods for such derivatization. Preferably, the formulations comprise beclomethasone dipropionate or its monohydrate. Beclomethasone dipropionate has the chemical name 9-chloro-11b,17,21-trihydroxy-16b-methylpregna-1,4-diene-3,20-doinel 7,21-dipropionate and the following structural formula:

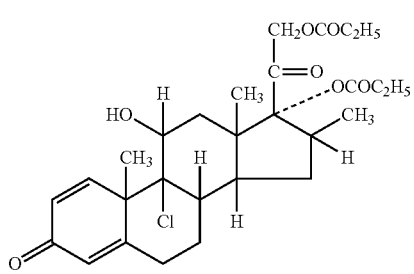

The compound may be a white powder with a molecular weight of 521.25; and is very slightly soluble in water (Physicians' Desk Reference.®), very soluble in chloroform, and freely soluble in acetone and in alcohol.

Particle Size Distribution Profile

The formulations of the present invention may comprise a cocorticosteroid (e.g., beclometasone diproprionate) having the following particle size distribution profile: about 10% or less of the drug substance particles have a particle size of less than 0.75 microns; about 25% or less of the drug substance particles have a particle size of less than 1.5 microns; about 50% or less of the drug substance particles have a particle size of less than 2.0 microns; about 75% or less of the drug substance particles have a particle size of less than 3.5 microns; about 90% or less of the drug substance particles have a particle size of less than 5.0 microns; and greater than 90% or about 100% of the drug substance particles have a particle size of less than 10 microns. Surprisingly, it has been discovered that formulations containing a cocorticosteroid (e.g., beclomethasone dipropionate) having a particle size distribution profile falling within the above ranges provide increased bioavailability over conventional formulations when administered via the intranasal route to a subject in need thereof, as well as increased and prolonged drug efficacy.

As used herein, particle size refers to an average particle size as measured by conventional particle size measuring techniques well known to those skilled in the art, such as sedimentation field flow fractionation, photon correlation spectroscopy, or disk centrifugation, among other techniques.

In an alternative embodiment, the formulation of the present invention comprises a drug substance having the following particle size distribution profile: about 10% of the drug substance particles have a particle size of less than 0.35 microns; about 25% of the drug substance particles have a particle size of less than 0.70 microns; about 50% of the drug substance particles have a particle size of less than 1.25 microns; about 75% of the drug substance particles have a particle size of less than 2.0 microns; about 90% of the drug substance particles have a particle size of less than 3.0 microns; and greater than 90% or about 100% of the drug substance particles have a particle size of less than 6.5 microns. Preferably, the drug substance is beclomethasone dipropionate.

The formulations of the present invention may also comprise a drug substance having the following particle size distribution profile: about 10% of the drug substance particles have a particle size less than 0.75, 0.70, 0.60, 0.55, 0.50, 0.40, 0.35, 0.30, 0.25, 0.20, 0.15, 0.10, or 0.05 microns; about 25% of the drug substance particles have a particle size less than 1.5, 1.45, 1.40, 1.35, 1.30, 1.25, 1.20, 1.15, 1.10, 1.05, 1.0, 0.95, 0.90, 0.85, 0.80, 0.75, 0.70, 0.65, 0.60, 0.55, 0.50, 0.45, 0.40, 0.35, 0.30, 0.25, 0.20, 0.15, or 0.10 microns; about 50% of the drug substance particles have a particle size less than 2.5, 2.4, 2.3, 2.2, 2.1, 2.0, 1.9, 1.8, 1.7, 1.6, 1.5, 1.4, 1.3, 1.2, 1.1, 0.9, 0.8, 0.7, or 0.6 microns. About 75% of the drug substance particles have a particle size less than 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, or 1.4 microns; about 90% of the drug substance particles have a particle size less than 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, or 2.1 microns and greater than 90% or about 100% of the drug substance particles have a particle size less than 10, 9.5, 9.0, 8.5, 8.0, 7.5, 7.0, 6.5, 6.0, 5.5, 5.0, 4.5, or 0.40 microns.

In one preferred embodiment, the formulation of the present invention comprises a drug substance having the following particle size distribution profile: about 10% of the drug substance particles have a particle size less than 0.40 microns; about 25% of the drug substance particles have a particle size less than 0.70 microns; about 50% of the drug substance particles have a particle size less than 1.3 microns; about 75% of the drug substance particles have a particle size less than 2.0 microns; about 90% of the drug substance particles have a particle size less than 3.0 microns; greater than 90% or about 100% of the drug substance particles have a particle size less than 6.0 microns.

In another alternative embodiment, the formulation of the present invention comprises a drug substance having the following particle size distribution profile: about 10% of the drug substance particles have a particle size less than 0.60 microns; 25% of the drug substance particles have a particle size less than 0.90 microns; about 50% of the drug substance particles have a particle size less than 1.5 microns; about 75% of the drug substance particles have a particle size less than 2.5 microns; about 90% of the drug substance particles have a particle size less than 3.5 microns; greater than 90% or about 100% of the drug substance particles have a particle size less than 6.0 microns.

In another alternative embodiment, greater than 90% or about 100% of the particles have a particle size less than 15 microns, preferably less than 10 microns, more preferably less than 8 microns, most preferably less than 7 microns. In another preferred embodiment, greater than 90% or about 100% of the particles have a particle size between 4 and 7 microns or 5 and 6 microns. In another embodiment, greater than 90% or about 100% of the particles have a particle size less than 10 microns, preferably less than 7 microns; less than 6 microns; less than 5 microns, or less than 4 microns.

In one alternative embodiment, such aqueous suspension formulations are suitable for direct administration to a subject via the nasal passages and represent an improvement over conventional techniques for administering the drug substances intranasally, particularly beclomethasone. Specifically, due to the specific particle size distribution profile of the drug substance, the present formulations provide increased bioavailability of the drug substance as well as increased efficacy and/or prolonged therapeutic effect of the drug substance.

The formulation of the present invention may be provided as an aqueous suspension. As used herein, suspension include, but are not limited to, mixtures of fine, non-settling particles of a solid within a liquid phase. In one embodiment, the formulation of the present invention is an aqueous suspension comprising about 0.005% to about 10% w/w of a drug substance, calculated on a dry basis. In alternate embodiment, the drug substance is beclomethasone.

In another alternate embodiment, the formulation of the present invention is an aqueous suspension comprising about 0.005% to about 5%, or 0.01% to about 2.5% w/w of a drug substance, calculated on a dry basis. In a preferred embodiment, the formulation is an aqueous suspension comprising about 0.025% to about 1.0% w/w of a drug substance, calculated on a dry basis having the particular particle size distribution profile of the present invention, wherein the drug substance is preferably beclomethasone. Even more preferably, the formulation is an aqueous suspension comprising about 0.04% to about 0.05% w/w of a drug substance, calculated on a dry basis. In a preferred embodiment, the drug substance is beclomethasone dipropionate.

In a preferred embodiment, the formulation of the present invention is an aqueous suspension comprising about 0.042% by weight of beclomethasone dipropionate, calculated on a dry basis, wherein the beclomethasone dipropionate has the following particle size distribution range: about 10% of the particles have a particle size of less than 0.35 microns; about 25% of the particles have a particle size of less than 0.65 microns; about 50% of the particles have a particle size of less than 1.20 microns; about 75% of the particles have a particle size of less than 1.9 microns; about 90% of the particles have a particle size of less than 2.85 microns; and greater than 90% or about 100% of the particles have a particle size of less than 6.0 microns.

In one alternative embodiment, the nasal formulation of the present invention may comprise a preservative, suspending agent, wetting agent, tonicity agent and/or diluent. In one embodiment, the formulations provided herein may comprise from about 0.01% to about 90%, or about 0.01% to about 50%, or about 0.01% to about 25%, or about 0.01% to about 10%, or about 0.01% to about 5% of one or more pharmacologically suitable suspending fluids which is physiologically acceptable upon administration intranasally. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in inhaled drugs.

In certain embodiments herein, the formulations of the present invention have a pH of about 2.0 to about 9.0. Optionally, the formulations of the present invention may contain a pH buffer. For example, a buffer may comprise any known pharmacologically suitable buffers which are physiologically acceptable upon administration intranasally. The buffer may be added to maintain the pH of the formulation between about 3.0 and about 7.0, for example.

Sterility or adequate antimicrobial preservation may be provided as part of the present formulations. Since certain formulations of the present invention are intended to be administered intranasally, it is preferred that they be free of pathogenic organisms. A benefit of a sterile liquid suspension is that it reduces the possibility of introducing contaminants into the individual when the suspension formulation is administered intranasally, thereby reducing the chance of an opportunistic infection. Processes which may be considered for achieving sterility may include any appropriate sterilization steps known in the art. In one embodiment, the drug substance (e.g., beclomethasone) is produced under sterile conditions, the micronization is performed in a sterile environment, and the mixing and packaging is conducted under sterile conditions. In alternative embodiment, the formulations of the present invention may be sterile filtered and filled in vials, including unit dose vials providing sterile unit dose formulations which are used in a nasal spray device for example. Each unit dose vial may be sterile and is suitably administered without contaminating other vials or the next dose. In one alternative embodiment, one or more ingredients in the present formulation may be sterilized by steam, gamma radiation or prepared using or mixing sterile steroidal powder and other sterile ingredients where appropriate. Also, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for inhalation safety, as the treated tissues may be sensitive to irritants. Preservatives suitable for use herein include, but are not limited to, those that protect the solution from contamination with pathogenic particles, including phenylethyl alcohol, benzalkonium chloride, benzoic acid, or benzoates such as sodium benzoate. Preferably, the preservative for use in the present formulations is benzalkonium chloride or phenylethyl alcohol. In certain embodiments, the formulations herein comprise from about 0.01% and about 1.0% w/w of benzalkonium chloride, or from about 0.01% and about 1% v/w phenylethyl alcohol. Preserving agents may also be present in an amount from about 0.01% to about 1%, preferably about 0.002% to about 0.02% by total weight or volume of the composition.

The formulations provided herein may also comprise from about 0.01% to about 90%, or about 0.01% to about 50%, or about 0.01% to about 25%, or about 0.01% to about 10%, or about 0.01% to about 1% w/w of one or more emulsifing agent, wetting agent or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methyl cellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract. In certain embodiments herein, the present formulations comprise polysorbate 80, microcrystalline cellulose, carboxymethylcellulose sodium and/or dextrose.

The present formulations may further comprise from about 0.01% to about 90%, or about 0.01% to about 50%, or about 0.01% to about 25%, or about 0.01% to about 10%, or about 0.01% to about 1% of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salt, citric acid, nitrilotriacetic acid and the salts thereof. In another embodiment, particularly in the suspension formulations provided herein, the complexing agent is sodium edetate. In one embodiment, the compositions contain sodium edetate at a concentration of about 0.05 mg/mL to about 0.5 mg/mL, or about 0.1 mg/mL to about 0.2 mg/mL. Also, for example, the formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulations provided herein also may comprise about 0.01% to about 90%, or about 0.01% to about 50%, or about 0.01% to about 25%, or about 0.01% to about 10%, or about 0.01% to about 10% of one or more solvents or co-solvents to increase the solubility of any of the components of the present formulation. Solvents or co-solvents for use herein include, but are not limited to, hydroxylated solvents or other pharmaceutically-acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. The preferred diluent is water.

Tonicity agents may include, but are not limited to, sodium chloride, potassium chloride, zinc chloride, calcium chloride and mixtures thereof. Other osmotic adjusting agents may also include, but are not limited to, mannitol, glycerol, and dextrose or mixtures thereof. In an alternative embodiment, the present formulation may comprise about 0.01% to about 10% w/w, or about 1% to about 8% w/w, or 1% to about 6% w/w, preferably about 5.0% w/w. The preferred tonicity agent is Dextrose, anhydrous.

In one alternative embodiment, the formulations of the present invention are stable. As used herein, the stability of formulations provided herein refers to the length of time at a given temperature that greater than 80%, 85%, 90% or 95% of the initial amount of drug substance, e.g., beclometbasone, is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25°. Also, in another alternative embodiment, using Arrhenius Kinetics, more than 80%, or more than 85%, or more than 90%, or more than 95% of the initial amount of drug substance (e.g., beclomethasone) remains after storage of the formulations for more than 1, 2, 12, 18, 24 or 36 months between about 15° C. and about 30° C.

The formulations of the present invention may be manufactured in any conventional manner by thoroughly mixing the ingredients described herein at ambient or elevated temperatures in order to achieve solubility of ingredients where appropriate.

The preparation of a drug substance having the particle size distribution profile of the present invention may be obtained by any conventional means known in the art, or by minor modification of such means. For example, suspensions of drug particles can rapidly undergo particulate size reduction when subjected to "jet milling" (high pressure particle in liquid milling) techniques. Other known methods for reducing particle size into the micrometer range include mechanical milling, the application of ultrasonic energy and other techniques.

In one alternative embodiment, the present invention provides a method for the treatment of rhinitis comprising the step of administering to a subject in need thereof a therapeutically effective amount of the formulations disclosed herein. In one embodiment, the method of the present invention comprises administering to a subject in need thereof a therapeutically effective amount of drug substance, wherein the drug substance is beclomethasone, the drug substance having a particle size distribution profile described herein. Preferably, the drug substance is beclomethasone dipropionate. In certain embodiments, the subject is a mammal. In other embodiments, the subject is a human.

In one embodiment, the present invention provides a method for treating rhinitis comprising the step of administering to a subject in need thereof a therapeutically effective amount of the present formulation, wherein the formulation comprises an aqueous suspension comprising about 0.005% to about 5% by weight of beclomethasone having a particle size distribution profile described herein. In certain embodiments, the formulation is sterile, contains a preservative and/or is stable.

In other embodiments, the present invention provides a method for treating rhinitis comprising the step of administering the formulations disclosed herein intranasally to a subject in need thereof. Preferably, the formulation is administered to a subject via nasal spray, preferably a metered-dose spray pump. The metered-dose spray pump may be manually operated, such that each actuation of the pump delivers a single dosage of the drug substance to the subject. In another embodiment, the formulation of the present invention may be administered via a nasal spray pump or atomizing spray pump.

In another alternative embodiment, the nasal spray comprises a metered-dose, manual pump spray unit (e.g. metering atomizing pump) comprising a microcrystalline suspension of beclometbasone dipropionate, monohydrate equivalent to 0.02% to about 2.0%, preferably about 0.10% to about 0.05%, more preferably about 0.042% w/w beclomethasone dipropionate, calculated on a dried basis, in an aqueous medium. In another alternative embodiment, said suspension comprises microcrystalline cellulose, carboxymethyl cellulose sodium, dextrose, benzalkonium chloride, polysorbate 80, and 0.25% v/w phenylethyl alcohol. An acid, preferably hydrochloric acid, may be added to adjust pH. The pH may be between 4.5 and 7.0. After initial priming (3-4 actuations), each actuation of the manual pump may deliver from a nasal adapter about 10 mg to about 1,000 mg, preferably about 100 mg to about 500 mg, most preferably about 100 mg of suspension containing beclomethasone dipropionate, monohydrate equivalent to about 10 mcg to about 500 mcg, or about 10 mcg to about 100 mcg, or about 30 mcg to about 60 mcg, preferably about 40 mcg to about 50 mcg, more preferably about 42 mcg of beclomethasone dipropionate, calculated on a dry basis. Each bottle containing the present formulations of nasal spray may provide about 20-600 metered doses, preferably 100 to about 300 doses, more preferably at least 200 metered doses.

In an alternative embodiment, the administration of the present formulations may comprise 1, 2, 3, 4, 5, 6, 7 or 8 inhalations of the present formulation in each nostril one, two, three, four or five times a day. Each inhalation may comprise about 1 mcg to about 400 mcg, or about 1 mcg to about 100 mcg, preferably about 30 mcg to about 100 mcg, more preferably about 30 mcg to about 80 mcg, or about 30 mcg to about 50 mcg most preferably about 42 mcg. The total dose per day of the drug substance may comprise about 10 mcg and about 4000 mcg, about 10 mcg to about 1,000 mcg, about 10 mcg to about 500 mcg, or about 100 mcg to about 900 mcg preferably about 100 mcg to about 500 mcg, or more preferably about 150 mcg to about 400 mcg.

In another alternative embodiment, the administration of the present formulations may comprise 1 and only 1 inhalation in each nostril a day. In one alternative embodiment, the starting dosage of the present formulation may comprise one and only 1 inhalation in each nostril once daily. In another alternative embodiment, such starting dosage is appropriate for adults. Each inhalation may comprise about 5 mcg to about 100 mcg, preferably from about 30 mcg to 70 mcg, more preferably about 42 mcg of beclomethasone, calculated on a dry basis.

Administering 1 and only 1 inhalation in each nostril is more beneficial and advantageous over conventional regimens of the prior art, which require more inhalations in each nostril per day. For example, other known nasal spray products, e.g., beclomethasone products, require 1 or 2 inhalations (42 to 84 mcg) in each nostril twice a day (total dose, 168-336 mcg/day). In contrast, formulations of the present invention may require 1 and only 1 inhalation in each nostril a day. By limiting the dosage, or amount of inhalations per day, individuals would likely comply with the regimen or regular dosage schedule to achieve adequate relief, thereby improving the patient's quality of life as compared with other traditional treatments. Further, administering fewer inhalations provide the individual more opportunity to take other medications during treatment, such as, for example, other oral or inhaled steroids, thus reducing likelihood of overdosing or cross reaction between medications. Further, providing fewer inhalations would reduce the likelihood of addiction to the drug substance in the nasal formulation. Moreover, administering fewer inhalations may reduce toxicity and the adverse events associated with 2 or more inhalations of a particular drug substance in each nostril per day. Also, individuals hypersensitive to 2 or more doses of a particular drug substance would benefit from receiving 1 and only 1 dose per day.

The present formulations can be packaged as kits or systems, which optionally contain other components, including instructions for use of the formulations. Articles of manufacture, containing packaging material and a formulation provided herein, which is useful for treatment, prevention or amelioration of one or more symptoms of a medical condition, disorder or disease (e.g. rhinitis) and a label indicating that the formulation is used for treatment, prevention or amelioration of one or more symptoms of diseases or disorders associated with undesired and/or uncontrolled rhinitis.

VI. EXAMPLE

The following example is included for illustrative purposes only and is not intended to limit the scope of the invention.

A double-blind, double-dummy, randomized, placebo-controlled, study was performed to assess the safety and efficacy of the formulations of the present invention (Dey BD), in adolescent and adult patients with seasonal allergic rhinitis. The objectives of this study were (1) to determine the safety and efficacy of Dey BD compared with placebo during 2 weeks of treatment in adult and adolescent patients with seasonal allergic rhinitis (SAR); and (2) to establish the comparability of Dey BD with Beconase AQ® Nasal Spray during 2 weeks of treatment in adults and adolescent patients. Currently, Beconase AQ® is commercially available from Glaxo-SmithKlein.

Both Dey and Beconase AQ® comprised a microcrystalline suspension of beclomethasone dipropionate, monohydrate equivalent to 0.042% w/w beclomethasone dipropionate, calculated on a dried basis, in an aqueous medium. However, the beclomethasone used in Dey BD nasal spray was derived and/or purchased from a different source from that used in Beconase AQ®. Otherwise, both nasal sprays contained the same excipients and additives in the same amounts. Also, Dey BD nasal spray and Beconase AQ® was administered by the same metered-dose, manual pump spray. For both the BD nasal spray and Beconase AQ®, each activation of the manual pump delivered about 42 mcg of beclomethasone dipropionate.

The study was conducted during the 2001 fall allergy season (local fall pollen) in the United States. The study duration was 3 weeks and consisted of 2 phases: a 1-week baseline screening period followed by a 2-week randomized double-blind treatment phase. Patients were seen on an outpatient basis on Day -7, Day 1, Day 7, and Day 14. Initial baseline assessments occurred 1 week prior (Day -7±2 days) to randomization to treatment. Patients were first assigned a patient number and then screened for eligibility based on study entrance criteria and completion of baseline assessments. If eligible, patients were then given standard oral antihistamine as a rescue medication and a Patient Total Nasal Symptom Score (TNSS) Diary. Patients recorded daily TNSS (sum of the signs and symptoms for runny nose, nasal congestion, sneezing, and itchy nose) in their diaries rating each on a scale of zero to 3 with zero being no symptoms present and 3 being severe symptoms present, as well as the amount of oral antihistamine taken. One week later, at the conclusion of the baseline assessments, the patients returned to the study site and were re-evaluated for eligibility. Patients who did not complete the diaries or no longer met the inclusion/exclusion criteria were discontinued.

To be included in the study, patients must have been diagnosed with SAR and must have met the following inclusion criteria:
  At least a 2-yr history of moderate-to-severe SAR due to fall pollen;
  Individuals 12 years of age and older;
  Confirmed IgE-mediated hypersensitivity to local fall pollen within last 12 months (a positive result is required);
  Minimum TNSS of 8 of a maximum of 12 on at least 3 days during the baseline period, one of which must have been within 3 days of Day 1;
  If receiving immunotherapy, a stable maintenance regimen for 30 days prior to study enrollment;
  General good health and free of disease or concomitant treatment that could interfere with interpretation of study results;
  Written informed consent/pediatric assent; and,
  Willingness to comply with study procedures.

Patients who met all criteria were then randomized to 1 of 5 treatment groups: (1) Dey BD Nasal Spray (0.042%) Low Dose—1 spray of Bottle 1 (Dey BD) in each nostril followed by 1 spray of Bottle 2 (placebo) in each nostril twice daily (morning and evening); (2) Dey BD Nasal Spray (0.042%) High Dose—1 spray of Bottle 1 (Dey BD) in each nostril followed by 1 spray of Bottle 2 (Dey BD) in each nostril twice daily (morning and evening); (3) Beconase AQ® Low Dose—1 spray of Bottle 1 (Beconase AQ®) in each nostril followed by 1 spray of Bottle 2 (placebo) in each nostril twice daily (morning and evening); (4) Beconase AQ® High Dose—1 spray of Bottle 1 (Beconase AQ®) in each nostril followed by 1 spray of Bottle 2 (Beconase AQ®) twice daily (morning and evening); and (5) placebo—1 spray of Bottle 1 (placebo) in each nostril followed by 1 spray of Bottle 2 (placebo) in each nostril twice daily (morning and evening).

The double-blind treatment phase (Day 1 through 14) consisted of twice daily self-administered treatment (1 spray from each bottle into each nostril per administration). On Days 7 and 14 (or at early termination), patients returned to the study sites and were evaluated. Efficacy assessments included reflective and instantaneous TNSS daily diary information, patient and physician global evaluations, and use of rescue medication.

The primary endpoint for this study was the change from baseline in a patient's 12-hour (AM and PM combined) reflective TNSS over a 2-week treatment period. The primary endpoint analysis was the comparison of Dey BD High Dose versus placebo. TNSS consisted of the sum of the 12-hour assessment scores for runny nose, nasal congestion, sneezing, and itchy nose recorded twice daily on the Patient's TNSS Diary card. Baseline was defined as the average of the run-in period 12-hour (AM plus PM combined) reflective TNSS from the 7 calendar days ±2 days preceding Day 1.

The secondary endpoints for this study were as follows:
The change from baseline in a patient's combined AM plus PM 12-hour reflective TNSS overall (Days 2-14);
The change from baseline in a patient's combined AM plus PM 12-hour reflective TNSS at Days 7 and 14;
The change from baseline in a patient's AM 12-hour reflective TNSS;
The change from baseline in a patient's PM 12-hour reflective TNSS;
The change from baseline to 1-week and 2-week postbaseline in area under the concentration curve (AUC)s of patient's combined AM plus PM 12-hour reflective TNSS;
The change from baseline to 1-week and 2-week postbaseline in AUC of patient's AM 12-hour reflective TNSS;
The change from baseline to 1-week and 2-week postbaseline in AUC of patient's PM 12-hour reflective TNSS;
The change from baseline in patient's AM plus PM combined instantaneous TNSS;
The change from baseline in patient's AM instantaneous TNSS;
The change from baseline in patient's PM instantaneous TNSS;
Patient global evaluation of change in SAR signs and symptoms;
Physician global evaluation of change in SAR signs and symptoms; and,
Use of rescue medication.

Secondary efficacy endpoints were compared across all treatment groups.

With respect to efficacy, both reflective and instantaneous change from baseline in 12-hour (AM plus PM, combined and individual) TNSS for primary and secondary variables at Week 1 and Week 2 were compared across the groups using a mixed effect analysis of variance (ANOVA) model. Area under the curve (AUC) of the 12-hour (AM plus PM, combined and individual) reflective TNSS was calculated for the baseline period and Week 1 and Week 2 (over Days 2-14) postbaseline using a trapezoidal method. The change from baseline was compared across the groups using a similar ANOVA model. The patient's and physician's global evaluation of change from baseline in SAR symptoms was compared between the groups using a one-way ANOVA model. Frequency of rescue medication use, as well as the percentage of patients needing rescue medication, was compared across the groups using Fisher's exact test. The average number of tablets of rescue medication was compared using an ANOVA model. All statistical analyses were performed for both Intent-to-Treat (ITT) and per-protocol populations. Missing observations in the ITT Population were imputed using the last observation carried forward (LOCF) method. All inferential statistics were conducted against a two-sided alternative hypothesis at 0.05 level of significance.

A total of 674 patients were randomized to 1 of 5 treatment groups (136 Dey BD High Dose, 136 Dey BD Low Dose, 135 Beconase AQ® High Dose, 129 Beconase AQ® Low Dose, or 138 placebo groups); 661 (98.07%) patients completed the study and 13 (1.93%) patients discontinued. The most common reasons for discontinuation were AE and withdrawal of consent (4/13 patients each, 30.77%). More than 85% of the patient population was White, more than 60% were female with a mean age across groups ranging from 33.62 to 36.79 years and a mean antigen challenge result ranging from 8.6 to 9.4 mm. The majority of patients had a negative history of beclomethasone usage (mean range=82.61-87.60%).

All active treatment groups (Dey BD and Beconase AQ®) demonstrated reductions in TNSS over the 2-week treatment period. Regardless of which efficacy endpoint was examined (i.e., 12-hour reflective TNSS, instantaneous TNSS, change in AUC), the Treatment effect was highly significant as was the Day effect (p=0.0000) indicating improvement in TNSS. Both Dey BD and Beconase AQ® High Dose groups were statistically superior to placebo for both primary and secondary efficacy endpoint analyses, as were Dey BD Low Dose and Beconase AQ® Low Dose treatment groups. Treatment-by-Day interaction (overall Days 2-14) and Treatment-by-Week interaction effects were not statistically significant indicating that the treatment groups behaved similarly for the duration of the study, except for the magnitude of improvement in TNSS. There was no statistical difference between Dey BD and Beconase AQ® High Dose groups for any efficacy endpoint analysis. However, the Dey BD Low Dose group was found to be consistently statistically superior to the Beconase AQ® Low Dose group in relieving symptoms of SAR. Results of analyses for the Per Protocol Population paralleled those of the ITT Population for all efficacy variables.

Figure 2:
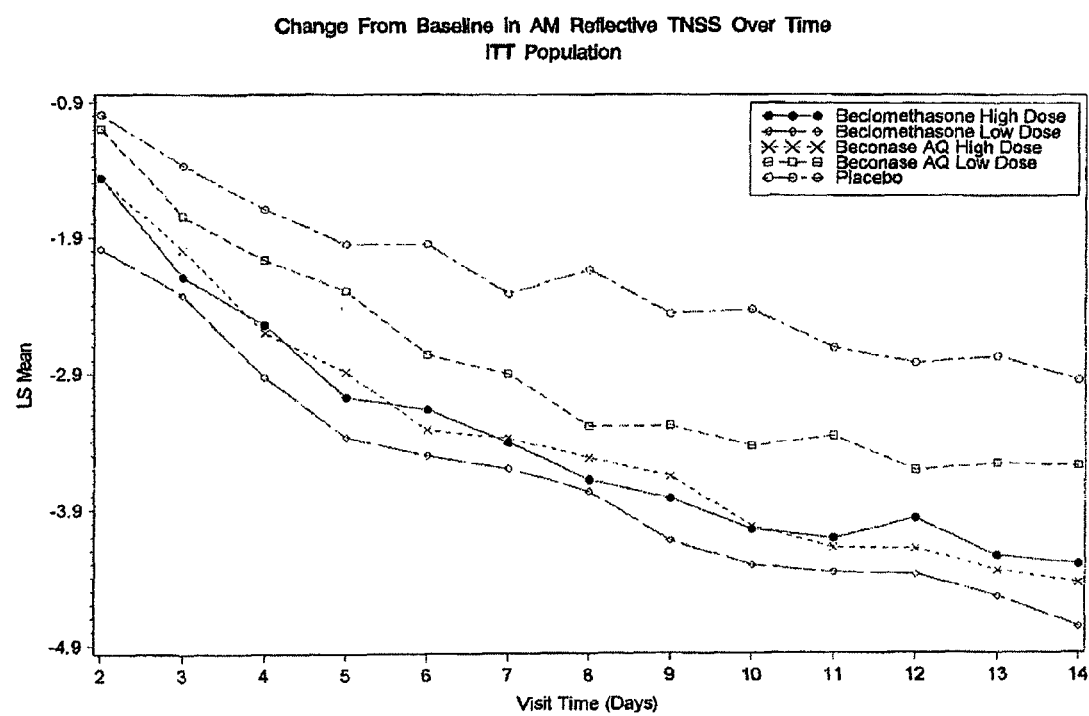
FIG. 2 shows the change from baseline in AM reflective TNSS over time in the ITT population over a 14 day study period.
Figure 3:
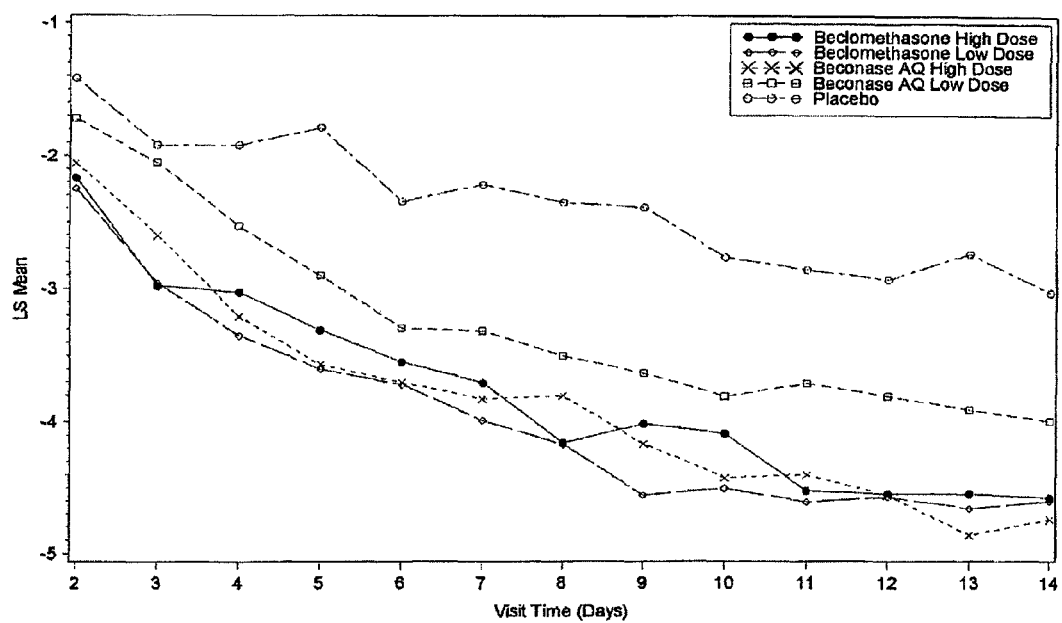
FIG. 3 shows the change from baseline in PM reflective TNSS over time in the ITT population over a 14 day study period.
Figure 4:
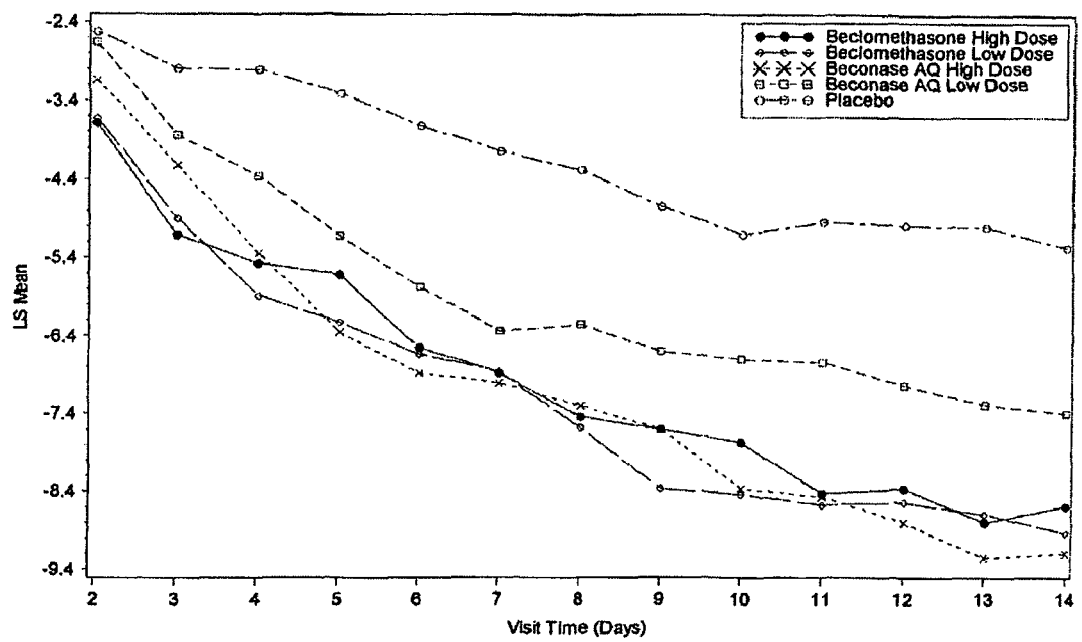
FIG. 4 shows the change from baseline in AM and PM reflective TNSS over time in the PP population over a 14 day study period.

FIG. 1 shows the change from baseline in AM and PM reflective TNSS over time in the ITT population over the 14 day study period. FIG. 2 shows the change from baseline in AM reflective TNSS over time in the ITT population over the 14 day study period. FIG. 3 shows the change from baseline in PM reflective TNSS over time in the ITT population over the 14 day study period. FIG. 4 shows the change from baseline in AM and PM reflective TNSS over time in the PP population over the 14 day study period.

In FIGS. 1-4, the efficacy of the nasal formulations is expressed as the change from baseline (pretreatment) in a composite score of nasal symptoms (e.g. runny nose, sneezing, nasal itching and congestion) referred to as total nasal symptom scores (TNSS). The change from baseline in TNSS scores is expressed in absolute units (rather tan percent change from baseline). Using an analysis of variance model (ANOVA), the least square mean (LS Mean) for the baseline (positive value) and change from baseline (negative value if symptoms improve) are obtained. The higher the negative value seen in the LS Mean, the greater was the change (improvement) in TNSS.

Table 1 shows the particle size distribution of the beclomethasone particles in Dey BD, wherein the particle size is in microns. Table 2 shows the quantitative composition of Dey BD.

TABLE 1

Dey BD Nasal Spray Particle Size Data

| | Run 1 | Run 2 | Run 3 | Avg |
|---|---|---|---|---|
| D (v, 0.10) | 0.29 | 0.27 | 0.32 | 0.29 |
| D (v, 0.25) | 0.58 | 0.54 | 0.58 | 0.57 |
| D (v, 0.50) | 1.15 | 1.10 | 1.06 | 1.10 |
| D (v, 0.75) | 1.84 | 1.81 | 1.81 | 1.82 |
| D (v, 0.90) | 2.73 | 2.60 | 2.75 | 2.69 |
| D (v, 1.00) | 5.69 | 5.69 | — | 5.69 |

TABLE 2

Quantitative Composition of Beclomethasone Dipropionate Monohydrate Nasal Spray, 0.042%

| Component | Function | Concentration in Drug Product | Amount per Spray* | Amount per Bottle** | Amount per Kilogram |
|---|---|---|---|---|---|
| Beclomethasone Dipropionate Monohydrate, USP | Active Ingredient | 0.042% w/w• | 42 μg• | 11 mg• | 0.42 g• |
| Benzalkonium Chloride Solution, 50%, NF | Preservative | 0.020% w/w•• | 20 μg•• | 5.3 mg•• | 0.20 g•• |
| Microcrystalline Cellulose/Carboxymethylcellulose Sodium, NF | Suspending Agent | 1.50% w/w• | 1.50 mg• | 398 mg• | 15.0 g• |
| Polysorbate 80, NF | Wetting Agent | 0.0050% w/w | 5.0 μg | 1.3 mg | 0.050 g |
| Phenylethyl Alcohol, USP | Preservative | 0.25% v/w | 255 μg••• | 68 mg••• | 2.6 g••• |
| Dextrose, anhydrous, USP | Tonicity Agent | 5.000% w/w | 5.000 mg | 1.325 g | 50.00 g |
| Hydrochloric Acid, 1N | To adjust pH | as required | as required | as required | as required |
| Purified Water, USP | Diluent | N/A | 93.18 mg | 24.69 g | 931.5 g |

V/w = volume to weight;
w/w = weight to weight
•Dry Basis
••Expressed as Benzalkonium Chloride
•••Based on Density of 1.019 g PEA/mL
*Target Spray Weight = 100 mg
**Target Fill = 26.5 g per Bottle The Figures and attachments herein are presented for illustrative purposes only. They are not intended to limit the scope of the invention. Further, it should be understood that various changes and modifications to the presently preferred embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements or steps described herein. Further, the invention described herein suitably may comprise or be practiced in the absence of any element or step which is not specifically disclosed herein. Further, one or more step described herein may be performed simultaneously with another step.

What is claimed is:

1. A method of treating one or more symptoms of rhinitis comprising the steps of applying to an individual's nasal mucosa a microcrystalline suspension of beclomethasone particles suspended in an aqueous medium, said suspension comprising about 0.01% to about 1% of beclomethasone and having the following particle size distribution:
   about 10% of the beclomethasone particles have a particle size of less than 0.3 microns;
   (ii) about 25% of the beclomethasone particles have a particle size of less than 0.55 microns;
   (iii) about 50% of the beclomethasone particles have a particle size of less than 1.1 microns;
   (iv) about 75% of the beclomethasone particles have a particle size of less than 1.8 microns; and
   (v) about 90% of the beclomethasone particles have a particle size of less than 2.7 microns;
   wherein the suspension is suitable for administration to the nasal mucosa of an individual.

2. The method of claim 1, wherein the microcrystalline suspension of beclomethasone particles suspended in an aqueous medium is sterile.

3. The method of claim 1, wherein the microcrystalline suspension of beclomethasone particles suspended in an aqueous medium further comprises a preservative.

4. The method of claim 1, wherein the microcrystalline suspension of beclomethasone particles suspended in an aqueous medium is stable.

5. The method of claim 1, wherein the microcrystalline suspension of beclomethasone particles suspended in an aqueous medium is applied to the individual's nasal mucosa from a metered-dose spray pump bottle.

6. The method of claim 1, wherein the microcrystalline suspension of beclomethasone particles suspended in an aqueous medium comprises about 0.04% to about 0.045% by weight of beclomethasone.

7. The method of claim 1, wherein the microcrystalline suspension of beclomethasone particles suspended in an aqueous medium comprises about 0.042% w/w beclomethasone disproportionate, calculated on a dried basis, in an aqueous medium.

8. The method of claim 1, wherein the microcrystalline suspension of beclomethasone particles suspended in an aqueous medium further comprises one or more of the following compounds:
(a) microcrystalline cellulose;
(b) carboxymethyl cellulose sodium;
(c) dextrose;
(d) benzalkonium chloride;
(e) polysarbate 80; and
phenylethyl alcohol.

* * * * *

UNITED STATES PATENT AND TRADEMARK OFFICE
CERTIFICATE OF CORRECTION

PATENT NO. : 8,158,154 B2
APPLICATION NO. : 11/931424
DATED : April 17, 2012
INVENTOR(S) : Chaundry Page 1 of 1

It is certified that error appears in the above-identified patent and that said Letters Patent is hereby corrected as shown below:

Column 9,
Line 58, "beclometbasone" should read --beclomethasone--.

Column 10,
Line 54, "beclometbasone" should read --beclomethasone--.

Column 16,
Line 14, before "about 10%" insert --(i)--.

Column 18,
Line 10, before "phenylethyl alcohol" insert --(f)--.

Signed and Sealed this
Twenty-second Day of January, 2013

David J. Kappos
*Director of the United States Patent and Trademark Office*